(12) United States Patent
Tortora

(10) Patent No.: US 11,719,693 B2
(45) Date of Patent: *Aug. 8, 2023

(54) SYSTEM AND METHOD FOR DETECTING PATHOGENS ON TREATED AND UNTREATED SUBSTRATES USING LIQUID CRYSTAL CHROMONIC AZO DYE

(71) Applicant: Pathogen Systems, Inc., Broomfield, CO (US)

(72) Inventor: Luana Tortora, Stow, OH (US)

(73) Assignee: Pathogen Systems, Inc., Broomfield, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/996,172

(22) Filed: Jun. 1, 2018

(65) Prior Publication Data
US 2018/0275070 A1    Sep. 27, 2018

Related U.S. Application Data

(62) Division of application No. 14/941,351, filed on Nov. 13, 2015, now Pat. No. 10,656,148.

(60) Provisional application No. 62/079,019, filed on Nov. 13, 2014.

(51) Int. Cl.
| | | |
|---|---|---|
| *G01N 33/543* | (2006.01) | |
| *G01N 21/77* | (2006.01) | |
| *G01N 21/23* | (2006.01) | |

(52) U.S. Cl.
CPC ....... *G01N 33/54373* (2013.01); *G01N 21/23* (2013.01); *G01N 21/77* (2013.01); *G01N 33/54313* (2013.01)

(58) Field of Classification Search
CPC ....... G01N 33/54373; G01N 33/54313; G01N 21/77; C12Q 1/04
See application file for complete search history.

(56) References Cited

U.S. PATENT DOCUMENTS

| | | | | |
|---|---|---|---|---|
| 3,833,287 | A * | 9/1974 | Taylor ................. | G02F 1/13737 349/165 |
| 10,495,636 | B2 * | 12/2019 | Tortora ............ | G01N 33/54393 |
| 2002/0052002 | A1 * | 5/2002 | Niehaus ............... | G01N 33/551 435/7.1 |
| 2004/0185551 | A1 * | 9/2004 | Niehaus ........... | G01N 33/54373 435/287.2 |
| 2009/0226639 | A1 * | 9/2009 | Lavrentovich ......... | C09K 19/02 428/1.2 |
| 2011/0141431 | A1 * | 6/2011 | Jordan .................... | G01N 21/21 349/199 |
| 2016/0085010 | A1 * | 3/2016 | Shin ..................... | G02B 5/3083 428/195.1 |
| 2016/0085071 | A1 * | 3/2016 | Border ............... | G02B 27/0172 359/485.05 |
| 2020/0225219 | A1 * | 7/2020 | Tortora ............ | G01N 33/54313 |

* cited by examiner

*Primary Examiner* — Melanie Brown
(74) *Attorney, Agent, or Firm* — Glenn H. Lenzen; Elevated IP, LLC

(57) ABSTRACT

Chromonic azo dyes are particular types of chromonic molecules that are alignable homeotropically (aggregated molecules stack perpendicularly to the surface) on different types of substrates, often without the need of any special surface treatment. This feature enables the optimization of a detection device with increased sensitivity based of the alignment distortion created by a biological immune complex.

7 Claims, 5 Drawing Sheets

Prior Art
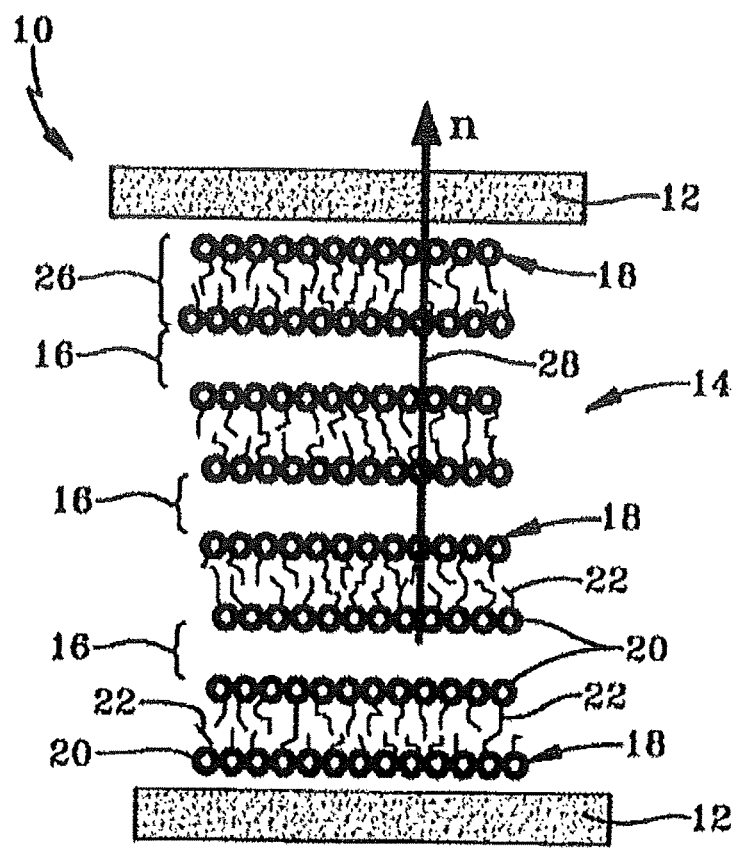
FIG. 1.A
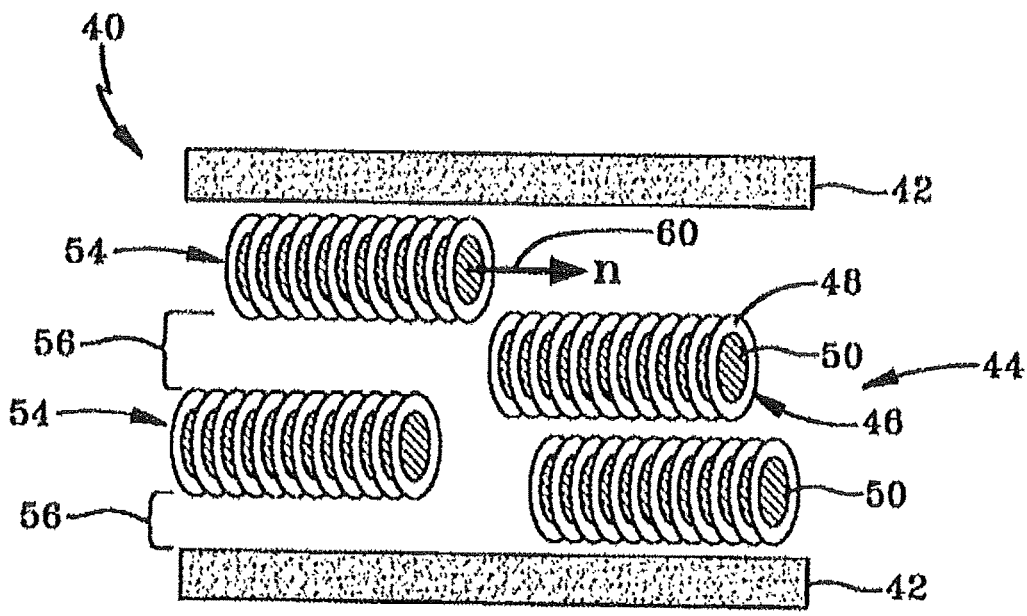
FIG. 1.B

SYSTEM AND METHOD FOR DETECTING PATHOGENS ON TREATED AND UNTREATED SUBSTRATES USING LIQUID CRYSTAL CHROMONIC AZO DYE

CROSS-REFERENCE TO RELATED APPLICATIONS

This Application is a divisional patent application of and claims priority to U.S. patent application Ser. No. 14/941,351, filed on Nov. 13, 2015, which claims the benefit of U.S. Provisional Patent Application Ser. No. 62/079,019 filed on Nov. 13, 2014, the entire contents of which are incorporated herein in their entirety by reference.

FIELD OF THE INVENTION

The present invention relates generally to the detection of pathogens and other toxic substances. More specifically, the present invention relates to a detection device with an amplification system comprised of a liquid crystal chromonic azo dye aligned homeotropically in a closed cell for the rapid detection of a ligand.

BACKGROUND OF THE INVENTION

A liquid crystal is a state of the matter intermediate a solid and an isotropic liquid and characterized by long range orientation order and reduced or absent positional order. Liquid crystals can be divided into thermotropic, lyotropic and metallotropic categories. Thermotropic and lyotropic liquid crystals consist of organic molecules, while metallotropic liquid crystals comprise both organic and inorganic molecules. Thermotropic materials exhibit a phase transition into the liquid crystalline phase as a function of temperature change. In lyotropic liquid crystals, phase transitions are a function of both temperature and concentration of the molecules in a solvent. In the case of metallotropic mesophases, the phase transition depends not only on temperature and concentration, but also on the inorganic-organic composition ratio.

A special class of lyotropic liquid crystals of a non-surfactant nature exists which is known as lyotropic chromonic liquid crystals, for convenience referred to hereinafter as "LCLC." This family of organic molecules is broad and includes pharmaceutical drugs and dyes. Chromonic molecules are considered lyotropic because they form a liquid crystal phase when in solution with an appropriate solvent, generally water. However they are quite different from a typical amphiphilic molecule (such as a surfactants molecule) that is characterized by a polar head and a flexible hydrophobic tail: chromonic liquid crystals have a disk-like or plank-like shape, with a relatively rigid aromatic core and ionic groups at the periphery.

Both amphiphilic and chromonic molecules aggregate in solution. Surfactant-based lyotropic liquid crystals aggregate forming micelles, while chromonic molecules tend to stack face to face, forming polydisperse, rod-like aggregates [J. Lydon, Chromonics, in: Handbook of Liquid Crystals [Wiley-VCH, Weinheim, 1998) v. 2B, p. 981 and Current Opin. Col. Inter. Sci. 3, 458 (1998)]. The aggregation is driven by weak non-covalent interactions such as π-π attraction, and the length of the aggregates depends on concentration and temperature.

Alignment techniques allow controlling the orientation of liquid crystals on substrates treated with aligning materials such as polyimides. Unidirectional rubbing on polyimide-coated substrates is a standard means of aligning thermotropic liquid crystals in the display industry. Chromonics may be aligned using this technique. A specific alignment direction (parallel or perpendicular) of the liquid crystal with respect to the substrate is achieved by choosing polyimides with different properties. Lyotropic surfactant-based liquid crystals usually self-align when placed between two parallel glass plates. The alignment orientation is dictated by the molecules' interaction with the surface and it is generally homeotropic, which means that the director is oriented perpendicular to the bounding plates.

DISCUSSION OF PRIOR ART

Although both thermotropic and surfactant-based liquid crystals are relatively easy to align they are also quite toxic materials for biologicals [*Liquid Crystals* 32(4):417-423, 2005]. The non-surfactant nature of chromonic molecules and low toxicity makes them suitable for biological applications such as biosensors where the liquid crystals are used as amplification system. Prior detection technologies involving liquid crystals are disclosed in U.S. Pat. Nos. 6,171,802 B1; 7,745,220 B2; 6,411,354 B1; and U.S. Pat. No. 6,570,632 B2.

An exemplary prior art detection technology having a surfactant-based lyotropic liquid crystal cell is designated generally by the numeral 10 in FIG. 1.A. The cell 10 includes a pair of opposed substrates 12, which are sealed in a well-known manner, and that contain surfactant-based lyotropic liquid crystal material designated generally by the numeral 14. The material 14 is formed using water 16 as a solvent for amphiphilic molecules 18, characterized by polar (hydrophilic) parts 20 and apolar (hydrophobic) parts 22. When water 16 is added to amphiphilic molecules 18, such as the cationic surfactant Cetylpyridinium Chloride [$C_{21}H_{38}NCl$], a bilayer 26 forms as the hydrophobic regions coalesce to minimize interaction with the water 16 while enhancing the polar component's interaction with water. The molecules on average are oriented along the direction schematically shown by a thick vertical arrow 28 called the director n. On average, the surfactant molecules are oriented along the director n. Surfactant molecules, and thus the director n, orient normally perpendicular to the bounding plates 12 (so-called homeotropic orientation). The detection is achieved by the introduction of a receptor into the liquid crystal matrix. In the presence of a ligand and the resultant formation of a complex, an optically detectable local deformation of the alignment is created. Most biologic receptors possess both hydrophilic and hydrophobic regions and thus can in principle incorporate into lyotropic liquid crystals. However, the quality of such incorporation depends on the particular hydrophobic hydrophilic balance in the system. Moreover, the surfactant environment might harm the detected biological species.

An exemplary prior art detection technology having a non-surfactant lyotropic chromonic liquid crystal cell is designated generally by the numeral 40 in FIG. 1.B. The cell 40 includes a pair of opposed substrates 42, which are sealed in a well-known manner that contains lyotropic liquid crystal material 44. Qualitatively, the difference from the surfactant type lyotropic materials is that LCLC molecules, designated generally by the numeral 46, are disc-like or plank-like rather than rod-like. The polar hydrophilic parts 48 form the periphery of each molecule, while the central core 50 is relatively hydrophobic. This distinction creates a range of different ordered structures. Individual disc-like molecules may form cylindrical aggregates 54 in water 56.

The direction of average molecular orientation is defined by the orientation of the normals to the planes of the plank-like or disc-like molecule. In other words, a director 60 is along the axis of the cylindrical aggregate and shows the direction n of orientation.

In the example depicted in FIG. 1.B, the long axes of the aggregates are oriented in a direction parallel to the bounding plates. However, the aggregates do not necessarily align in the same parallel direction. Such an alignment requires a special treatment of the substrates. An efficient detection of ligands is possible when the liquid crystal is aligned uniformly in the liquid crystal cell and the ligand-receptor pairs disturb this uniform alignment. Furthermore, detection based on planar alignment of liquid crystals requires a specific orientation of the liquid crystal cell when viewed through cross polar lenses for an efficient detection.

Chromonic liquid crystals can be aligned homeotropically on glass, but a surface treatment is still needed with an aligning material [Langmuir, 30 (10), 2914-2920, 2014; PRL 105, 017801, 2010; Soft Matter, 8, 8478-8482, 2012; Mol. Cryst. Liq. Cryst., 576, 2-7, 2013]. Alignment methods involve the use of precise manufacturing techniques and the application of relatively costly materials to cell substrates.

Thus, a need exists for an alternative simplified detection and amplification mechanism which does not involve the use of either thermotropic or surfactant-based liquid crystals, and which can be easily achieved using plain substrates without elaborate coating and rubbing of the alignment layer. Alternatively, a preferred system using minimal substrate treatment (such as quick-dry spray coatings) and not requiring a specific orientation of the liquid crystal cell when viewed through cross polar lenses may also be advantageously used in detection and amplification applications.

SUMMARY OF THE INVENTION

The present invention provides a system for the detection and amplification of ligands based on the homeotropic alignment of non-surfactant lyotropic chromonic liquid crystals.

The present invention further provides homeotropic alignment of lyotropic chromonic liquid crystals when sandwiched between a pair of uncoated substrates. Additionally, homeotropic alignment can be obtained by coating the substrates with hydrophobic, low surface energy materials.

In another embodiment, the present invention provides homeotropic alignment of lyotropic chromonic liquid crystal material, wherein the liquid crystal material is a chromonic azo dye.

In yet another embodiment, the present invention provides homeotropic alignment of lyotropic chromonic liquid crystal material, wherein the optimized concentration of liquid crystal in the carrier medium is in a preselected range.

In still another embodiment, the present invention provides homeotropic alignment of lyotropic chromonic liquid crystal material, wherein the liquid crystal is in the nematic phase in the temperature range.

In a further embodiment, the present invention provides homeotropic alignment of lyotropic chromonic liquid crystal material, wherein the alignment surfaces are materials such as but not limited to acrylics, COP and COC.

In another embodiment, the present invention provides homeotropic alignment of lyotropic chromonic liquid crystal material, wherein the alignment surfaces are glass substrates coated with hydrophobic low surface tension materials, which include, but it is not limited to, soluble low cure polyimides, super hydrophobic coatings, and acrylic sprays.

In yet another embodiment, the present invention provides homeotropic alignment lyotropic chromonic liquid crystal material when sandwiched between a pair of uncoated substrates which is very stable under manipulation and applied pressure.

In still another embodiment, the present invention provides homeotropic alignment, wherein the lyotropic liquid crystal material is mixed with a ligand/receptor biospecies and then disposed between the substrates and observed to determine whether the biospecies distorts alignment of the liquid crystal material.

BRIEF DESCRIPTION OF THE DRAWING

FIG. 1.A is a schematic cross-sectional view of a prior art surfactant-based liquid crystal cell;

FIG. 1.B is a schematic cross-sectional view of a prior art non-surfactant chromonic liquid crystal cell;

DESCRIPTION OF THE INVENTION

Figure 2:
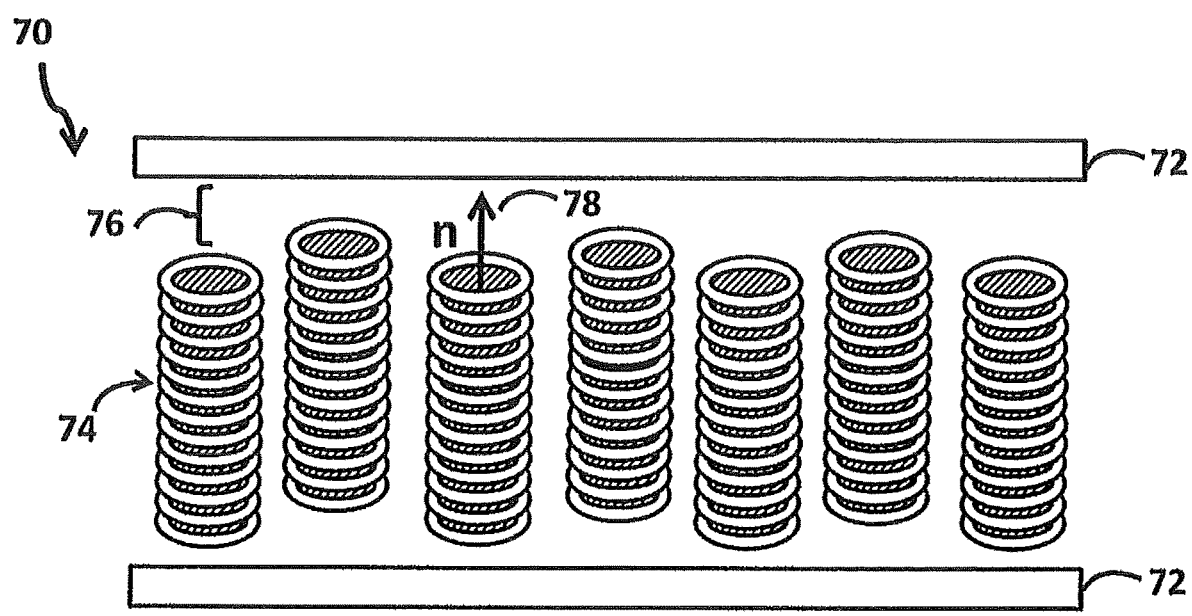
FIG. 2 is a schematic cross-sectional view of a lyotropic chromonic liquid crystal cell in accordance with an embodiment.

In the present invention a detection device or system based on homeotropic aligned non surfactant-lyotropic chromonic liquid crystal is presented. As best seen in FIG. 2, a lyotropic chromonic liquid crystal cell according to the present invention defining a contained space therein is designated generally by the numeral 70. The cell 70 includes a pair of opposed substrates or plates 72, which are sealed in a well-known manner in a cell (not shown) containing a lyotropic chromonic liquid crystal material 74 suspended in water 76 and contained within the cell 70 intermediate the substrates. The liquid crystal material contained in the cell forms a "nematic slab", a term used in the art. In accordance with an embodiment, a preferred range of the ratio in the water-azo dye solution is approximately 30-36% dye to water by weight. Unlike prior art materials such as, the chromonic material 44 of FIG. 1.B, wherein the opposed substrates are in preferential alignment with chromonic material 44, the material aggregates 74 are homeotropic with respect to a variety of substrates. Homeotropic means that the long axes of the liquid crystal aggregates are oriented in a direction perpendicular to the bounding plates. Director 78 shows the direction of orientation. Such an alignment often does not require any special treatment of the substrates.

Figure 3:
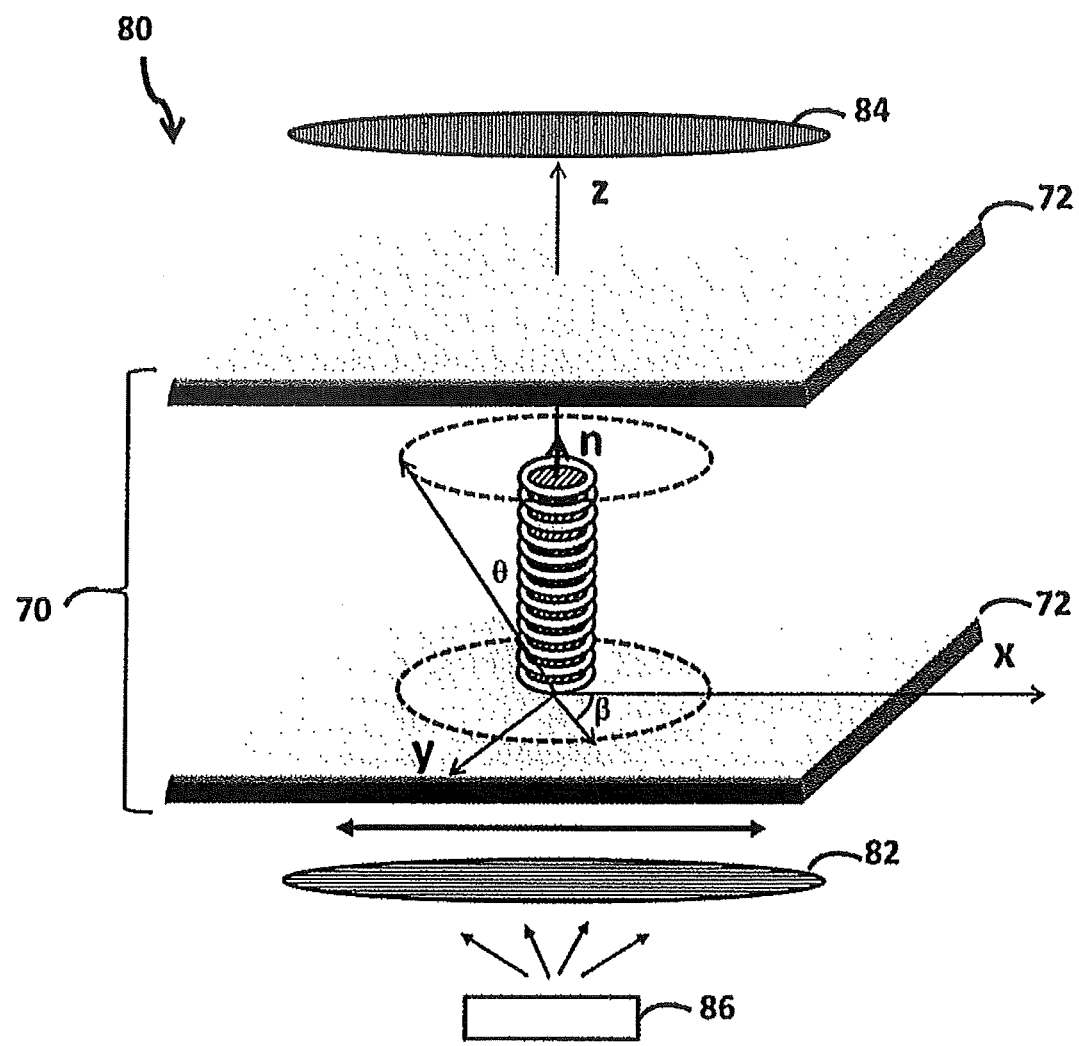
FIG. 3 is a side perspective view of a lyotropic chromonic liquid crystal cell coupled with a light source and at least one polarizer in accordance with an embodiment.

In the detection device or system designated generally by the numeral 80 and schematically shown in FIG. 3, the cell 70 is placed between two crossed polarizers or light analyzers 82, 84. A homeotropic aligned cell ideally has no direction, but is preferably oriented in a plane defined by first an x axis and second a y axis, the x and y axes being perpendicular to one another (the x-y plane) as shown. The system is rotationally symmetric. If a deformation is introduced, such as a receptor-ligand complex, the aggregates deviate at a certain angle from the perpendicular direction around the disturbance. Each of the crossed polarizers are positioned opposite one another outside of the cell and adjacent a respective one of the opposed substrates 72. A light beam from a light source 86 impinges on the cell, along the axis Z. A polarizer 82 placed between the light source 86 and the cell makes the impinging light linearly polarized.

The light intensity passed through a pair of crossed polarizers and a generic nematic slab having a thickness d positioned between them follows equation 1:

$$I = I_0 \sin^2 2\beta \sin^2 \frac{\pi d}{\lambda_0} \left( \frac{n_0 n_e}{\sqrt{n_e^2 \cos^2 \theta + n_0^2 \sin^2 \theta}} - n_0 \right) \quad \text{Eq. 1}$$

where $\theta$ is the angle the director n makes with the axis Z, $\beta$ is the angle between the in-plane horizontal projection of director n (or n if $\theta=\pi/2$) and the polarization of incident light; d is the thickness of the nematic slab, $\lambda_0$ is the wavelength in vacuum, $n_o$ and $n_e$ are respectively the ordinary and extraordinary optical refractive indexes of the liquid crystalline medium. A detector (not shown) is positioned on the side of the cell opposite the light source for detecting any light passing through the cell, as is known in the art.

When n is parallel to the z-axis (homeotropic orientation) $\theta=0$, I=0 and the sample appears dark when seen between cross polarizers. The dark condition, also referred to herein as "extinction", can be also obtained when $\theta \neq 0$ but $=0,\pi/2, \ldots$, such as, by way of example, the case of planar alignment, where the extinction is achieved by orienting the director along the polarization direction of the polarizer or the analyzer. However, if a distortion is introduced with the director varying from point to point, then the extinction condition is no longer satisfied and $I \neq 0$.

Figure 4:
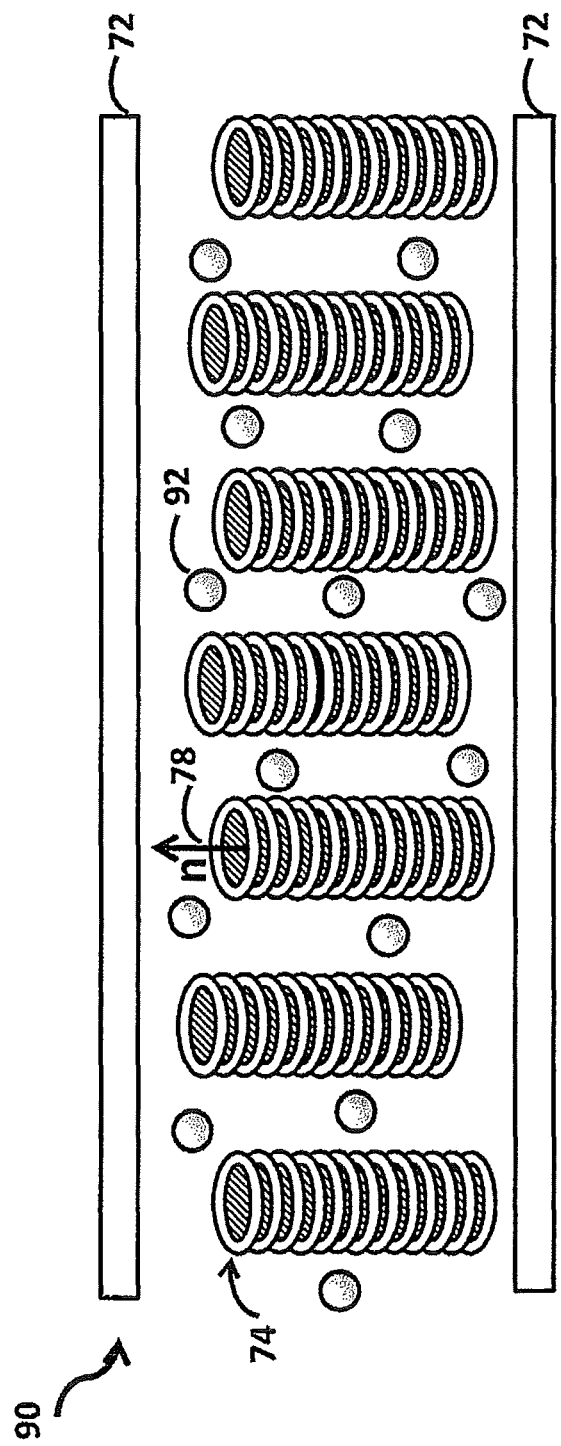
FIG. 4 is schematic cross-sectional view of a lyotropic chromonic liquid crystal cell without a detected material contained therein in accordance with an embodiment.
Figure 5:
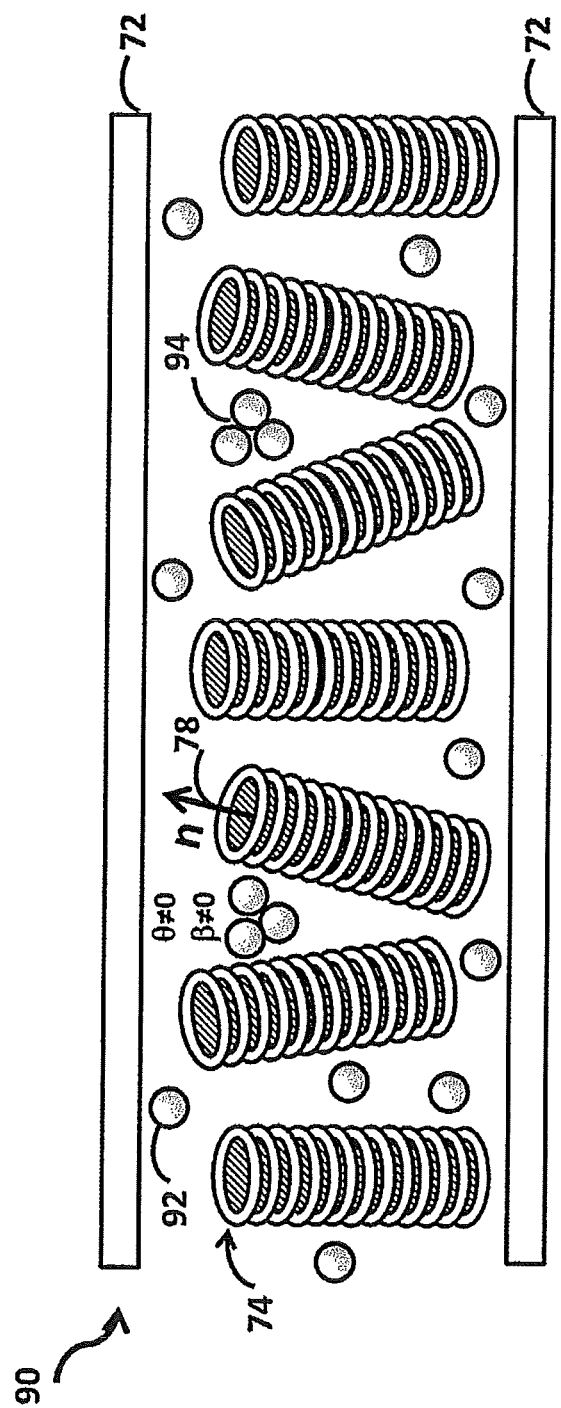
FIG. 5 is a schematic cross-sectional view of a lyotropic chromonic liquid crystal cell having a detected material contained therein in accordance with an embodiment.

In another embodiment of the present invention an exemplary non-surfactant lyotropic liquid crystal cell with homeotropic alignment used for the detection and amplification of ligands is shown schematically in FIG. 4 and designated generally by the numeral 90. The cell includes a pair of opposed substrates 72, such as ZEONEX® (a cyclo olefin polymer material developed by ZEON Corporation) plates, and a lyotropic chromonic liquid crystal material 74 suspended in water, oriented in such a way that the director is everywhere perpendicular to the cell substrates. The presence of small disturbance created by, for example, receptor 92, no disruption of this alignment exists. However, as seen in FIG. 5, in the presence of reactive ligand 94, a sufficiently large aggregated biological complex 96 is formed and the liquid crystal orientation is locally distorted with generation of detectable light transmission.

In one preferred embodiment of the present invention, a chromonic liquid crystal material 74 is mixed with a receptor 92, such as antibody coated micro-bead and a ligand 94 (a microbe), the mixture is injected with either positive or negative pressure between two substrates 72 assembled and sealed in a well-known manner as herein described; and the assembled cell is inserted in a detection device. Preferably, the detecting device, consists of a light source, two linear polarizers in crossed position and a photo detector. The position of the liquid crystal cell is in between the two polarizers. Binding of the ligand to the receptor induces the formation an antigen-antibody complex with consequent distortion of the aligned liquid crystal generating optically detectable birefringence. In other words, the incident polarized light entering the cell with local anisotropic distortion, splits into ordinary and extraordinary light waves, with mutually orthogonal polarizations, travelling at different speeds. Because the two components travel at different velocities, the propagated waves are out of phase. When the waves are recombined as they exit the liquid crystal cell, the polarization state of each has changed as a result of this phase difference. Thus, the linear polarized light becomes elliptically polarized and a light component then passes through the second polarized (analyzer) to the photo detector.

Example 1

Homeotropic Alignment on ZEONEX® Plastic Substrates

To make a cell of LCLC comprised of water solutions of chromonic azo dye, two ZEONEX® 350R cyclo olefin polymer plates are cut to size and assembled to create a cell with thickness controlled by glass spacers. A nematic water solution of chromonic azo dye is injected in the cassette at room temperature using positive pressure. After relaxation of transient stripe textures due to flow induced planar alignment, the LCLC spontaneously orients homeotropically on the uncoated substrates. These substrates proved to be suitable in aligning the chromonic azo dye in a homeotropic fashion, which is appropriate for applications such as the detection and amplification of ligands.

Example 2

Homeotropic Alignment on APEL™ APL5015AL Plastic Substrates

To make a cell of LCLC comprised of water solutions of chromonic azo dye, two APEL™ APL5015AL (a cyclo olefin copolymer material developed by Mitsui Chemicals, Inc.) plates are cut to size, and assembled to create a cell with thickness controlled by glass spacers. A nematic water solution of chromonic azo dye is injected in the cassette at room temperature using positive pressure. After relaxation of transient stripe textures due to flow induced planar alignment, the LCLC spontaneously orients homeotropically on the uncoated substrates. These substrates proved to be suitable in aligning the chromonic azo dye in a homeotropic fashion, which is appropriate for applications such as the detection and amplification of ligands.

Example 3

Homeotropic Alignment on ZEONOR® Films

To make a cell of LCLC comprised of water solutions of chromonic azo dye, ZEONOR® (a cyclo olefin polymer material developed by Zeon Corporation) films are laminated on glass, and assembled to create a cell with thickness controlled by glass spacers. A nematic water solution of chromonic azo dye is injected in the cassette at room temperature using positive pressure. After relaxation of a transient stripe textures due to flow induced planar alignment, the LCLC spontaneously orients homeotropically on the laminated films. These substrates proved to be suitable in aligning the chromonic azo dye in a homeotropic fashion, which is appropriate for applications such as the detection and amplification of ligands.

Example 4

Homeotropic Alignment on Low Cure Polyimide Films

To make a cell of LCLC comprised of water solutions of chromonic azo dye, polyimide sheets such as AK-PI or NEXOLVE™ (a polyimide material developed by NeXolve Holding Company) are laminated on glass and assembled to create a cell with thickness controlled by glass spacers. A nematic water solution of chromonic azo dye is injected in the cassette at room temperature using positive pressure. After relaxation of a transient stripe textures due to flow induced planar alignment, the LCLC spontaneously orients homeotropically on the laminated films. The polyimide can also be solubilized in NMP/Butyl CELLOSOLVE™ (a solvent developed by Dow, Inc.) solution and spin coated, flexo printed or spray coated on glass and flash dried on a hot plate. These substrates proved to be suitable in aligning the chromonic azo dye in a homeotropic fashion, which is appropriate for applications such as the detection and amplification of ligands.

Example 5

Homeotropic Alignment on Super-Hydrophobic Coating

To make a cell of LCLC comprised of water solutions of chromonic azo dye, HYDROFOE™ (a super hydrophobic coating developed by Lotus Leaf Coatings, Inc.) is spray coated or dip coated on glass and the substrates assembled to create a cell with thickness controlled by glass spacers. A nematic water solution of chromonic azo dye is injected in the cassette at room temperature using positive pressure. After relaxation of a transient stripe textures due to flow induced planar alignment, the LCLC spontaneously orients homeotropically on the super-hydrophobic coating. These substrates proved to be suitable in aligning the chromonic azo dye in a homeotropic fashion, which is appropriate for applications such as the detection and amplification of ligands.

Example 6

Homeotropic Alignment on KRYLON® Crystal Clear Acrylic

To make a cell of LCLC comprised of water solutions of chromonic azo dye, KRYLON® (a crystal clear acrylic developed by Krylon, Inc.) is spray coated on glass and the substrates assembled to create a cell with thickness controlled by glass spacers. A nematic water solution of chromonic azo dye is injected in the cassette at room temperature using positive pressure. After relaxation of a transient stripe textures due to flow induced planar alignment, the LCLC spontaneously orients homeotropically on the acrylic coating. These substrates proved to be suitable in aligning the chromonic azo dye in a homeotropic fashion, which is appropriate for applications such as the detection and amplification of ligands.

What is claimed is:

1. A system for detecting pathogens in a liquid comprising:
    a sealed cell oriented in a plane and having a preselected thickness, the cell including first and second perpendicular axes defining the orientation plane;
    a pair of untreated opposed substrates positioned within the cell;
    a nematic lyotropic chromonic liquid crystal material suspended at room temperature in a liquid contained within the cell intermediate the pair of opposed substrates and aligned homeotropically therewith, the ratio of the nematic lyotropic chromonic liquid crystal material and the liquid in which it is suspended falling within a preselected concentration range;
    a receptor mixed into the chromonic liquid crystal material contained within the cell intermediate the pair of opposed substrates of the system;
    a light source adapted to emit a beam of light passing through the cell along an axis substantially perpendicular to the plane;
    a pair of linear polarizers, each polarizer being arranged in a cross-polarizing relationship with respect to each other and located adjacent to one of the opposed substrates;
    a light detector adapted to detect any portion of the beam of light which is transmitted through the cell and the polarizers.

2. The detector system of claim 1 wherein the receptor comprises an antibody micro-bead and a liquid.

3. The detection system of claim 1 wherein each of the substrates comprises uncoated and untreated cyclo olefin polymer material.

4. The detection systems of claim 1 wherein each of the substrates comprises uncoated Apel APL5015ML material.

5. The detection system of claim 1 wherein the nematic lyotropic chromonic liquid crystal material comprises a solution of chromonic azo dye suspended in water.

6. The detection system of claim 5 wherein the concentration range of the nematic lyotropic chromonic liquid crystal is 30 to 36% chromonic azo dye to water by weight, whereby the nematic lyotropic chromonic liquid crystal forms at least one nematic slab that is homeotropically aligned with respect to the first and second perpendicular axes defining the orientation plane and each of the pair of untreated opposed substrates positioned within the cell.

7. The detection system of claim 6 wherein the system is rotationally symmetric.

* * * * *